United States Patent [19]
Breider et al.

[11] Patent Number: 5,489,607
[45] Date of Patent: Feb. 6, 1996

[54] USE OF ENADOLINE IN THE TREATMENT OF BENIGN PROSTATIC ENLARGEMENT

[75] Inventors: Michael A. Breider, Ann Arbor; Cynthia L. Courtney, Milan; Felix A. De La Iglesia; Alexander W. Gough, both of Ann Arbor; Alan L. Metz, Saline, all of Mich.

[73] Assignee: Warner-Lambert Company, Morris Plains, N.J.

[21] Appl. No.: 389,526

[22] Filed: Feb. 16, 1995

[51] Int. Cl.$^6$ .......... A61K 31/40; A61K 31/55; A61K 31/44; A61K 31/335; A61K 31/34

[52] U.S. Cl. .......... 514/409; 514/212; 514/278; 514/414; 514/462; 514/567

[58] Field of Search .......... 514/409, 212, 514/278, 414, 462, 567

[56] References Cited

U.S. PATENT DOCUMENTS

| | | | |
|---|---|---|---|
| 4,737,493 | 4/1988 | Horwell | 514/409 |
| 4,965,278 | 10/1990 | Horwell et al. | 514/409 |
| 5,063,242 | 11/1991 | Horwell et al. | 514/409 |
| 5,317,028 | 5/1994 | McKnight et al. | 514/409 |
| 5,369,120 | 11/1994 | Woodruff | 514/409 |

OTHER PUBLICATIONS

D. H. Peters, et al., *Drugs*, 1993, 46:1, 177–208.

J. Monda, et al., *Mayo Clinic Proc*, 1993, 68:670–679.

S. L. Robins, et al., *Pathologic Basis of Disease*, 1994, 5:1025–6.

*Primary Examiner*—Jerome D. Goldberg
*Attorney, Agent, or Firm*—Elizabeth M. Anderson

[57] ABSTRACT

The instant invention is a method of using known compounds, such as (−)-5α,7α,-8β-N-methyl-N-[ 7-(1-pyrrolidinyl)-1-oxaspiro[4.5]dec-8-yl]-4-benzofuranacetamide, as agents for treating benign prostatic hyperplasia.

3 Claims, No Drawings

USE OF ENADOLINE IN THE TREATMENT OF BENIGN PROSTATIC ENLARGEMENT

BACKGROUND OF THE INVENTION

The present invention is related to a method of using 7-(substituted)amino-8-((substituted)carbonyl)methylamino)-1-oxaspiro(4.5)decanes or pharmaceutically acceptable salts thereof as agents for treating benign prostatic hyperplasia. Enadoline, chemical name, (−)- 5α,7α,-8α-N-methyl-N-[7-(1-pyrrolidinyl)-1-oxaspiro[ 4.5]dec-8-yl]-4-benzofuranacetamide monohydrochloride, with the chemical structure

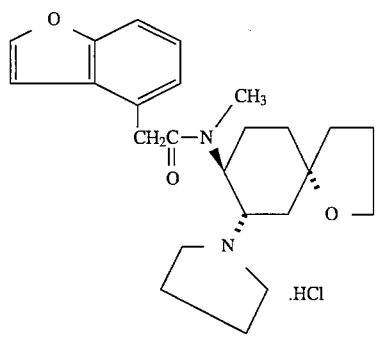

is especially effective. Enadoline, also known as CI-977, is a kappa-opioid agonist with analgesic properties which also causes sedation, diuresis, and elevation of corticosteroids.

U.S. Pat. No. 5,317,028 is related to a method of using 7-(substituted)amino-8 -((substituted)-carbonyl)-methylamino-1-oxaspiro(4.5)decanes and the pharmaceutically acceptable salts thereof as agents useful in treating Parkinson's disease, dystonia, and other movement disorders. The compounds, processed for preparing them, and pharmaceutical compositions containing them are found in U.S. Pat. No. 4,737,493, which is herein incorporated by reference. The disclosed utility in the patent is analgesic. The compounds are also disclosed as having sedative, diuretic, and corticosteroid elevating effects and therefore as being useful diuretic and psychotherapeutic agents.

U.S. Pat. No. 4,965,278 and its divisional U.S. Pat. No. 5,063,242 cover use of the above compounds for inflammation, stroke, and cerebrovascular disorders such as cerebral ischemia and infarction. These two patents are hereby incorporated by reference.

U.S. Pat. No. 5,369,120 relates to a pharmaceutical composition having synergistic effects using the above compounds and L-Dopa.

Benign enlargement of the prostate (nodular hyperplasia, benign prostatic hyperplasia/hypertrophy, BPH) is a common age-associated condition in humans. By age 60, it is estimated that 70% of men have prostatic nodular hyperplasia and that 50% of these men have symptoms related to prostatic enlargement. In both dogs and humans, development of prostatic enlargement is dependent on androgen exposure and dihydrotestosterone (DHT) is considered to be the principal mediator of prostatic hyperplasia. There appears to be an age-related propensity for DHT to accumulate in the prostate which may in part explain the high incidence of prostatic hyperplasia in the elderly. Symptoms associated with prostatic enlargement are considered secondary to either compression of the urethra with impairment of urination or retention of urine within the urinary bladder resulting in predisposition for development of urinary tract infection (S. L. Robins, et al, *Pathologic Basis Of Disease* 1994;5:1025–6).

The predominant treatment for symptomatic benign prostatic enlargement is transurethral prostatic resection. In fact, in males over 65 years of age, it is estimated that prostatic resection is second only to cataract extraction in number of surgical procedures performed each year. Due to the morbidity and expense associated with surgery, effective medical therapies are preferred.

Currently, there are two medical therapies for BPH: 5α-reductase inhibitors and α-adrenergic antagonists. Inhibition of 5α-reductase blocks the conversion of testosterone to DHT, thereby reducing androgenic stimulation for prostatic hyperplasia. Although 5α-reductase inhibitors, specifically finasteride, are well-tolerated, prolonged treatment (6–12 months) may be required to elicit beneficial effects (D. H. Peters, et al, *Drugs* 1993;46:177–208). The α-adrenergic antagonists provide symptomatic relief by reducing muscle tone in the urinary bladder and prostate, thereby decreasing resistance to urinary flow in the prostatic urethra (J. M. Monda, et al, *Mayo Clinic Proc* 1993;68:670–9). While both of these therapeutic approaches are useful, additional medical therapies which treat the underlying hyperplastic process and provide symptomatic relief within a shortened timeframe, will be valuable in treatment of BPH.

SUMMARY OF THE INVENTION

The present invention relates to a novel therapeutic means for treating benign prostatic hyperplasia which comprises administering to a patient in need of such treatment a therapeutically effective amount of a compound of Formula I as described hereinafter.

DETAILED DESCRIPTION OF THE INVENTION

The present invention provides certain substituted oxaspirodiaminocyclohexane compounds which are useful as agents for treating benign prostatic hyperplasia. The compounds are

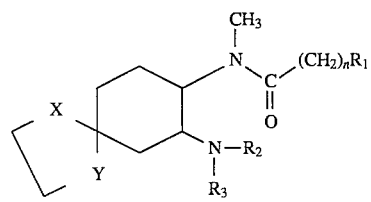

wherein n is an integer of from 1 to 6;
either of X or Y is oxygen and the other is —$CH_2$—;
$R_1$ is selected from

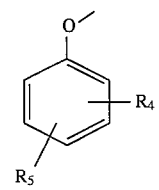

where $R_4$ and $R_5$ are independently hydrogen, fluorine, chlorine, bromine, nitro, trifluoromethyl, alkyl of from 1 to 6 carbon atoms, alkoxy of from 1 to 6 carbon atoms, or aryl;

b) 3,4,5-trimethylphenoxy;

c)

where $R_6$ is hydrogen, fluorine, chlorine, alkyl of from 1 to 6 carbon atoms, or aryl; Z is —$CH_2$—, —O—, —S—, or —$NR_7$— where $R_7$ is hydrogen, alkanoyl of from 1 to 6 carbon atoms, or alkyl of from 1 to 6 carbon atoms;

d)

where $R_8$ and $R_9$ are independently hydrogen, fluorine, bromine, alkyl of from 1 to 6 carbon atoms, or alkoxy of from 1 to 4 carbon atoms; or e)

where $R_8$ and $R_9$ are as defined above;
$R_2$ is methyl and $R_3$ is hydrogen, alkyl of from 1 to 6 carbon atoms, $-CH_2-\triangleleft$, $-CH_2CH:CH_2$, $-CH_2C\equiv CH$, $-CH_2CH_2-$[phenyl], $-CH_2CH_2-$[furanyl], $-CH_2CH_2-$[thienyl], or $-CH_2CH_2-N(-N=N)-C(=O)-NR_{10}$ where $R_{10}$ is alkyl of from 1 to 4 carbon atoms; or
where $R_2$ and $R_3$ when taken together with the nitrogen atom to which they are attached, form a pyrrolidinyl, piperidinyl, or hexahydro-1H-azepinyl ring; and the pharmaceutically acceptable acid addition salts thereof.

The compounds of the present invention constitute a class of derivatives of certain substituted oxaspirodiaminocyclohexane compounds of Formula I above in which 1 nitrogen atom is an amine nitrogen substituted with methyl and a second substituent selected from the group $R_3$ as defined above, or when taken together with the nitrogen atom to which they are attached, $R_2$ and $R_3$ form a pyrrolidinyl, piperidinyl, or hexahydro- 1H-azepinyl ring, and the other nitrogen atom is a N-methyl amide nitrogen further substituted with the group $R_1$ as defined above.

Compounds of the present invention contain one or more asymmetric carbon atoms and therefore exist in various stereoisomeric forms. Additionally, the compounds of this invention are capable of existing in different geometric isomeric forms. For example, the oxygen atom of the 5-membered spiro-ring may be positioned on the same side of the average plane of the cyclohexane ring as the amide nitrogen, or on the side opposite. The present invention contemplates all geometric and stereoisomeric forms of the compounds of Formula I above.

The individual stereoisomers are obtained, if desired, from mixture of the different forms by known methods of resolution such as the formation of diastereomers, followed by recrystallization.

Compounds of the instant invention include solvates, hydrates, and salts of Formula I above.

Preferred compounds of the present invention are those of Formula I above wherein $R_1$ is where $R_4$ and $R_5$ are independently hydrogen, fluorine, chlorine, bromine, nitro, trifluoromethyl, alkyl of from 1 to 6 carbon atoms, alkoxy of from 1 to 6 carbon atoms, or aryl.

By the term "aryl" is meant phenyl; phenyl substituted with fluorine, chlorine, alkyl of from 1 to 4 carbon atoms, nitro, or trifluoromethyl; 2- or 3-thienyl; and 2- or 3-thienyl substituted with alkyl of from 1 to 4 carbon atoms or alkoxy of from 1 to 4 carbon atoms.

Preferred compounds of the present invention are those of Formula I above where $R_1$ is wherein $R_6$ is as defined above. The most preferred compounds are substituted inden-1-yl compounds of Formula I above.

Other preferred compounds of the present invention are those of Formula I wherein $R_1$ is wherein $R_6$ is as defined above. The most preferred compounds are substituted benzofuran-4-yl compounds of Formula I.

Yet other preferred compounds of the present invention are those of Formula I wherein $R_1$ is wherein $R_6$ is as defined above. The most preferred compounds are substituted benzo[b]thiophen-4-yl compounds of Formula I.

Yet other preferred compounds of the present invention are those of Formula I wherein $R_1$ is wherein $R_6$ and $R_7$ are as defined above. The most preferred compounds are indol-4-yl compounds of Formula I.

Yet other preferred compounds of the present invention are those of Formula I wherein $R_1$ is

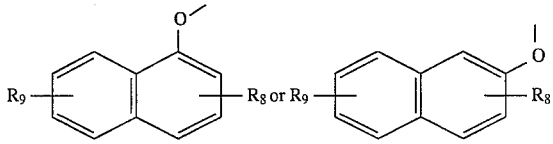

wherein $R_8$ and $R_9$ are independently hydrogen, fluorine, chlorine, bromine, alkyl of from 1 to 4 carbon atoms or alkoxy of from 1 to 4 carbon atoms.

Preferred substituents for $R_2$ and $R_3$ are those where $R_2$ is methyl and $R_3$ is lower alkyl, most preferably methyl, or where $R_2$ and $R_3$ taken together with the nitrogen atom to which they are attached form a pyrrolidinyl ring.

Preferred compounds of the present invention include but are not limited to:

[5R-(5α,7α,8β)]-N-Methyl-N-[7-(methyl-2-propynylamino)- 1-oxaspiro[4.5]dec -8-yl]-2-phenoxyacetamide,
[5S-(5α,7α,8β)]-N-Methyl-N-[7-(methyl-2-propynylamino)- 1-oxaspiro[4.5]dec -8-yl]-2-phenoxyacetamide,
[5R-(5α,7β,8α)]-N-Methyl-N-[7-(methyl-2-propynylamino)- 1-oxaspiro[4.5]dec -8-yl]-2-phenoxyacetamide,
[5s-(5α,7β,8α)]-N-Methyl-N-[7-(methyl-2-propynylamino)- 1-oxaspiro[4.5]dec -8-yl]-2-phenoxyacetamide,
[5R-(5α,7α,8β)]-2-(4-Fluorophenoxy)-N-methyl-N -[7-(1-pyrrolidinyl)]-1-oxaspiro[4.5]dec-8-yl]acetamide,
[5S-(5α,7α,8β)]-2-(4-Fluorophenoxy)-N-methyl-N -[7-(1-pyrrolidinyl)]-1-oxaspiro[4.5]dec-8-yl]acetamide,
[5R-(5α,7β,8α)]-2-(4-Fluorophenoxy)-N-methyl-N-[7-(1-pyrrolidinyl)]-1-oxaspiro[4.5]dec-8-yl]acetamide,
[5S-(5α,7β,8α)]-2-(4-Fluorophenoxy)-N-methyl-N-[7-(1-pyrrolidinyl)]-1-oxaspiro[4.5]dec-8-yl]acetamide,
[5R-(5α,7α,8β)]-2-(4-Fluorophenoxy)-N-methyl-N-[7-[methyl-(2-phenylethyl)amino]-1-oxaspiro[4.5]dec-[5R-(5α,7α,8β)]-2-(4-Fluorophenoxy)-N-methyl-N -8-yl]acetamide,
[5S-(5α,7α,8β)]-2-(4-Fluorophenoxy)-N-methyl-N -7-[methyl-(2-phenylethyl)amino]-1-oxaspiro[4.5]dec-8-yl]acetamide,
[5R-(5α,7β,8α)]-2-(4-Fluorophenoxy)-N-methyl-N -[7-[methyl-(2-phenylethyl)amino]-1-oxaspiro[4.5]dec-8-yl]acetamide,
[5S-(5α,7β,8α)]-2-(4-Fluorophenoxy)-N-methyl-N -[7-[methyl-(2-phenylethyl)amino]-1-oxaspiro[4.5]dec- 8-yl]acetamide,
[5R-(5α,7α,8β)]-N-Methyl-2-(3-nitrophenoxy)-N -[7-(1-pyrrolidinyl)-1-oxaspiro[4.5]dec-8-yl]acetamide,
[5S-(5α,7α,8β)]-N-Methyl-2-(3-nitrophenoxy)-N -[7-(1-pyrrolidinyl)-1-oxaspiro[4.5]dec-8-yl]acetamide,
[5R-(5α,7β,8α)]-N-Methyl-2-(3-nitrophenoxy)-N -[7-(1-pyrrolidinyl)-1-oxaspiro[4.5]dec-8-yl]acetamide,
[5S-(5α,7β,8α)]-N-Methyl-2-(3-nitrophenoxy)-N -[7-(1-pyrrolidinyl)-1-oxaspiro[4.5]dec-8-yl]acetamide,
[5R-(5α,7α,8β)]-N-Methyl-N-[7-(1-pyrrolidinyl)- 1-oxaspiro[4.5]dec-8-yl]-2-[3-(trifluoromethyl)phenoxy] acetamide,
[5S-(5α,7α,8β)]-N-Methyl-N-[7-(1-pyrrolidinyl)- 1-oxaspiro[4.5]dec-8-yl]-2-[3-(trifluoromethyl)phenoxy] acetamide,
[5R-(5α,7β,8α)]-N-Methyl-N-[7-(1-pyrrolidinyl)- 1-oxaspiro[4.5]dec-8-yl]-2-[3-(trifluoromethyl)phenoxy] acetamide,
[5S-(5α,7β,8α)]-N-Methyl-N-[7-(1-pyrrolidinyl)- 1-oxaspiro[4.5]dec-8-yl]-2-[3-(trifluoromethyl)phenoxy] acetamide,
[5R-(5α,7α,8β)]-2-(3,4-Dichlorophenoxy)-N-methyl-N-[7-(1-pyrrolidinyl)-1-oxaspiro[4.5]dec-8-yl]acetamide,
[5S-(5α,7α,8β)]-2-(3,4-Dichlorophenoxy)-N-methyl-N-[ 7-(1-pyrrolidinyl)-1-oxaspiro[4.5]dec-8-yl]acetamide,
[5R-(5α,7β,8α)]-2-(3,4-Dichlorophenoxy)-N-methyl-N-[7-(1-pyrrolidinyl)-1-oxaspiro[4.5]dec-8-yl]acetamide,
[5S-(5α,7β,8α)]-2-(3,4-Dichlorophenoxy)-N-methyl-N-[ 7-(1-pyrrolidinyl)-1-oxaspiro[4.5]dec-8-yl]acetamide,
[5R-(5α,7α,8β)]-2-(2,6-Dichlorophenoxy)-N-methyl-N-[ 7-(1-pyrrolidinyl)-1-oxaspiro[4.5]dec-8-yl]acetamide,
[5S-(5α,7α,8β)]-2-(2,6-Dichlorophenoxy)-N-methyl-N-[7-(1-pyrrolidinyl)-1-oxaspiro[4.5]dec-8-yl]acetamide,
[5R-(5α,7β,8α)]-2-(2,6-Dichlorophenoxy)-N-methyl-N-[7-(1-pyrrolidinyl)-1-oxaspiro[4.5]dec-8-yl]acetamide,
[5S-(5α,7β,8α)]-2-(2,6-Dichlorophenoxy)-N-methyl-N-[7-(1-pyrrolidinyl)-1-oxaspiro[4.5]dec-8-yl]acetamide,
[5R-(5α,7α,8β)]-2-(3,5-Dichlorophenoxy)-N-methyl-N-[7-(1-pyrrolidinyl)-1-oxaspiro[4.5]dec-8-yl]acetamide,
[5S-(5α,7α,8β)]-2-(3,5-Dichlorophenoxy)-N-methyl-N-[7-(1-pyrrolidinyl)-1-oxaspiro[4.5]dec-8-yl]acetamide,
[5R-(5α,7β,8α)]-2-(3,5-Dichlorophenoxy)-N-methyl-N-[7-(1-pyrrolidinyl)-1-oxaspiro[4.5]dec-8-yl]acetamide,
[5S-(5α,7β,8α)]-2-(3,5-Dichlorophenoxy)-N-methyl-N-[7-(1-pyrrolidinyl)-1-oxaspiro[4.5]dec-8-yl]acetamide,
[5R-(5α,7α,8β))]-N-Methyl-2-(1-naphthalenyloxy)-N-[ 7-(1-pyrrolidinyl)-1-oxaspiro[4.5]dec-8-yl]acetamide,
[5S-(5α,7α,8β)]-N-Methyl-2-(1-naphthalenyloxy)-N-[ 7-(1-pyrrolidinyl)-1-oxaspiro[4.5]dec-8-yl]acetamide,
[5R-(5α,7β,8α)]-N-Methyl-2-(1-naphthalenyloxy)-N-[7-(1-pyrrolidinyl)-1-oxaspiro[4.5]dec-8-yl]acetamide,
[5S-(5α,7β,8α)]-N-Methyl-2-(1-naphthalenyloxy)-N-[7-(1-pyrrolidinyl)-1-oxaspiro[4.5]dec-8-yl]acetamide,
[5R-(5α,7α,8β)]-N-Methyl-2-(2-naphthalenyloxy)-N-[ 7-(1-pyrrolidinyl)-1-oxaspiro[4.5]dec-8-yl]acetamide,
[5S-(5α,7α,8β)]-N-Methyl-2-(2-naphthalenyloxy)-N-[7-(1-pyrrolidinyl)-1-oxaspiro[4.5]dec-8-yl]acetamide,
[5R-(5α,7β,8α)]-N-Methyl-2-(2-naphthalenyloxy)-N-[7-(1-pyrrolidinyl)-1-oxaspiro[4.5]dec-8-yl]acetamide,
[5S-(5α,7β,8α)]-N-Methyl-2-(2-naphthalenyloxy)-N-[ 7-(1-pyrrolidinyl)-1-oxaspiro[4.5]dec-8-yl]acetamide,
[5R-(5α,7α,8β)]-N-Methyl-N-[7-[methyl[2-(2 -thienyl)ethyl]amino]-1-oxaspiro[4.5]dec-8-yl]-2-(1 -naphthalenyloxy)acetamide,
[5S-(5α,7α,8β)]-N-Methyl-N-[7-[methyl[2-(2 -thienyl)ethyl]amino]-1-oxaspiro[4.5]dec-8-yl]-2-(1 -naphthalenyloxy)acetamide,
[5R-(5α,7β,8α)]-N-Methyl-N-[7-[methyl[2-(2 -thienyl)ethyl]amino]-1-oxaspiro[4.5]dec-8-yl]-2-(1 -naphthalenyloxy) acetamide,
[5S-(5α,7β,8α)]-N-Methyl-N-[7-[methyl[2-(2 -thienyl)ethyl]amino]-1-oxaspiro[4.5]dec-8-yl]-2-(1 -naphthalenyloxy)acetamide,
[5R-(5α,7α,8β)]-N-Methyl-N-[7-(methyl-2-propenylamino)- 1-oxaspiro[4.5]dec-8-yl]-1H-indene-3-acetamide,
[5S-(5α,7α,8β)]-N-Methyl-N-[7-(methyl-2-propenylamino)- 1-oxaspiro[4.5]dec-8-yl]-1H-indene-3-acetamide,
[5R-(5α,7β,8α)]-N-Methyl-N-[7-(methyl-2-propenylamino)- 1-oxaspiro[4.5]dec-8-yl]-1H-indene-3-acetamide,
[5S-(5α,7β,8α)]-N-Methyl-N-[7-(methyl-2-propenylamino)- 1-oxaspiro[4.5]dec-8-yl]-i_H-indene-3-acetamide,
[5R-(5α,7α,8β)]-N-Methyl-[7-(1-pyrrolidinyl)-1-oxaspiro[ 4.5]dec-8-yl]-1H-indene-3-acetamide,
[5S-(5α,7α,8β)]-N-Methyl-[7-(1-pyrrolidinyl)-1-oxaspiro[ 4.5]dec-8-yl]-1H -indene -3-acetamide,

[5R-(5α,7β,8α)]-N-Methyl-[7-(1-pyrrolidinyl)-1-oxaspiro[4.5]dec-8-yl]-1H-indene-3-acetamide,

[5S-(5α,7β,8α)]-N-Methyl-[7-(1-pyrrolidinyl)-1-oxaspiro[4.5]dec-8-yl]-1H-indene-3-acetamide,

[5R-(5α,7α,8β)]-N-[7-(Dimethylamino)-1-oxaspiro[4.5]dec-8-yl]-N-methyl-1H-indole-3-acetamide,

[5S-(5α,7α,8β)]-N-[7-(Dimethylamino)-1-oxaspiro[4.5]dec-8-yl]-N-methyl-1H-indole-3-acetamide,

[5R-(5α,7β,8α)]-N-[7-(Dimethylamino)-1-oxaspiro[4.5]dec-8-yl]-N-methyl-1H-indole-3-acetamide,

[5S-(5α,7β,8α)]-N-[7-(Dimethylamino)-1-oxaspiro[4.5]dec-8-yl]-N-methyl-1H-indole-3-acetamide,

[5R-(5α,7α,8β)]-N-Methyl-N-[7-(1-pyrrolidinyl)-1-oxaspiro[4.5]dec-8-yl]-1H-indole-3-acetamide,

[5S-(5α,7α,8β)]-N-Methyl-N-[7-(1-pyrrolidinyl)-1-oxaspiro[4.5]dec-8-yl]-1H-indole-3-acetamide,

[5R-(5α,7β,8β)]-N-Methyl-N-[7-(1-pyrrolidinyl)-1-oxaspiro[4.5]dec-8-yl]-1H-indole-3-acetamide,

[5S-(5α,7β,8α)]-N-Methyl-N-[7-(1-pyrrolidinyl)-1-oxaspiro[4.5]dec-8-yl]-1H-indole-3-acetamide,

[5R-(5α,7α,8β)]-N-Methyl-N-[7-(1-pyrrolidinyl)-1-oxaspiro[4.5]dec-8-yl]-2-benzofuranacetamide,

[5S-(5α,7α,8β)]-N-Methyl-N-[7-(1-pyrrolidinyl)-1-oxaspiro[4.5]dec-8-yl]-2-benzofuranacetamide,

[5R-(5α,7β,8α)]-N-Methyl-N-[7-(1-pyrrolidinyl)-1-oxaspiro[4.5]dec-8-yl]-2-benzofuranacetamide,

[5S-(5α,7β,8α)]-N-Methyl-N-[7-(1-pyrrolidinyl)-1-oxaspiro[4.5]dec-8-yl]-2-benzofuranacetamide,

[5R-(5α,7α,8β)]-N-Methyl-N-[7-(1-pyrrolidinyl)-1-oxaspiro[4.5]dec-8-yl]-3-benzofuranacetamide,

[5S-(5α,7β,8α)]-N-Methyl-N-[7-(1-pyrrolidinyl)-1-oxaspiro[4.5]dec-8-yl]-3-benzofuranacetamide,

[5R-(5α,7β,8α)]-N-Methyl-N-[7-(1-pyrrolidinyl)-1-oxaspiro[4.5]dec-8-yl]-3-benzofuranacetamide,

[5S-(5α,7β,8α)]-N-Methyl-N-[7-(1-pyrrolidinyl)-1-oxaspiro[4.5]dec-8-yl]-3-benzofuranacetamide,

[5R-(5α,7α,8β)]-N-Methyl-N-[7-(1-pyrrolidinyl)-1-oxaspiro[4.5]dec-8-yl]-4-benzofuranacetamide,

[5S-(5α,7α,8β)]-N-Methyl-N-[7-(1-pyrrolidinyl)-1-oxaspiro[4.5]dec-8-yl]-4-benzofuranacetamide,

[5S-(5α,7β,8α)]-N-Methyl-N-[7-(1-pyrrolidinyl)-1-oxaspiro[4.5]dec-8-yl]-4-benzofuranacetamide,

[5R-(5α,7α,8β)]-N-[7-[(Cyclopropylmethyl)methylamino]-1-oxaspiro[4.5]dec-8-yl]-N,2-dimethyl-3-benzofuranacetamide,

[5S-(5α,7α,8β)]-N-[7-[(Cyclopropylmethyl)methylamino]-1-oxaspiro[4.5]dec-8-yl]-N,2-dimethyl-3-benzofuranacetamide,

[5R-(5α,7α,8β)]-N-[7-[(Cyclopropylmethyl)methylamino]-1-oxaspiro[4.5]dec-8-yl]-N,2-dimethyl-3-benzofuranacetamide,

[5S-(5α,7β,8α)]-N-[7-[(Cyclopropylmethyl)methylamino]-1-oxaspiro[4.5]dec-8-yl]-N,2-dimethyl-3-benzofuranacetamide.

More preferred compounds of the present invention include but are not limited to:

(−) (5α,7α,8β)-N-methyl-N-[7-pyrrolidinyl)-1-oxaspiro[4.5]dec-8-yl]-4-benzo[b]furacetamide, and (−)-(5α,7α,8β)-N-7-(1-pyrrolidinyl)-1-oxaspiro[4.5]dec-8-yl]-4-benzo[b]thiophene-4-acetamide.

The compounds of Formula I of the present invention have a very high kappa opioid affinity, selectivity and potency. For example, (−)-(5α-7α-8β)-N-methyl-N-[7-(1-pyrrolidinyl)-1-oxaspiro[4.5]dec-8-yl]-4-benzo[b]furanacetamide gives a Ki of 0.73 nM with a μ/kappa ratio of 798. The $MPE_{50}$ in the rat paw pressure test for analgesia is 0.030 (iv). This is considerably better than other selective kappa opioid compound known to the inventors.

Materials and Methods

Groups of 3 male Beagle dogs were given CI-977 orally (lactose mixture in gelatin capsules) at doses of 0, 50, 200, or 600 μg/kg/day for 4 weeks. At the end of the treatment period, all dogs were humanely euthanatized and prostates were removed and weighed. Body weights and brain weights were used for calculation of prostate:body weight and prostate:brain weight ratios. Following weighing, prostates were fixed in 10% neutral-buffered formalin for subsequent microscopic evaluation.

In a second study, groups of 3 male Beagle dogs were given CI-977 by continuous intravenous infusion (saline vehicle) for 4 weeks at doses of 0, 1, 5, or 35 μg/kg/hour. At the end of the treatment period, all dogs were humanely euthanatized. Prostate weights, weight ratios, and microscopy were done as for oral administration.

Results

Following oral administration of CI-977 for 4 weeks, absolute group mean prostate weights were decreased 46% to 57%, relative to control (Table I). There were proportional reductions in relative prostate weights (prostate:body weight, prostate:brain weight). Prostatic atrophy was noted microscopically in all dogs given CI-977. Atrophy was characterized by decreased size of glandular acini and decreased height of lining epithelial cells. Relative to dogs given 50 μg/kg, prostatic atrophy appeared accentuated at 200 and 600 μg/kg, however, there was no clear dose relationship to this effect. Microscopic slides of prostate were subsequently blind-coded and reevaluated without knowledge of dose group identification. This blinded histologic review confirmed the presence of prostatic atrophy in dogs given CI-977.

Relative to vehicle controls, group mean prostate weights were reduced 42% to 51% in dogs given CI-977 by continuous intravenous infusion for 4 weeks (Table I). Lack of statistical significance for reductions in prostatic weights following intravenous infusion of CI-977 was likely due to high interanimal variation in prostatic weights within the vehicle control group. Reductions in prostatic weights were, however, considered biologically significant and correlated with microscopic, prostatic glandular/epithelial atrophy which was similar to that noted following oral administration. Blinded histologic review of prostate sections confirmed the presence of prostatic atrophy in all dogs given CI-977. As with oral administration, severity of prostatic atrophy did not appear dose-related.

TABLE I

Prostate Weights Following Oral Administration of CI-977 for 4 Weeks

| Parameter | 0 μg/kg | 50 μg/kg | 200 μg/kg | 600 μg/kg |
|---|---|---|---|---|
| Prostate Wt (g) | 8.6 + 0.12 | 4.5 + 0.20** | 3.7 + 0.68** | 4.6 + 0.57** |
| Prostate Wt (g)/ | 0.068 + 0.0077 | 0.037 + 0.0003** | 0.029 + 0.0038** | 0.041 + 0.0049* |

TABLE I-continued

| 100 (g) Body Wt Prostate Wt (g)/ Brain Wt (g) | 0.111 + 0.0047 | 0.061 + 0.0029** | 0.048 + 0.0111** | 0.058 + 0.0065** |
|---|---|---|---|---|

| Prostate Weights Following Continuous Intravenous Infusion of CI-977 for 4 Weeks | | | | |
|---|---|---|---|---|
| Parameter | 0 µg/kg/hr | 1 µg/kg/hr | 5 mg/kg/hr | 35 µg/kg/hr |
| Prostate Wt (g) | 10.7 + 2.88 | 6.0 + 0.80 | 5.2 + 0.48 | 6.2 + 1.55 |
| Prostate Wt (g)/ 100 (g) Body Wt | 0.096 + 0.0188 | 0.054 + 0.0071 | 0.046 + 0.0035 | 0.055 + 0.0116 |
| Prostate Wt (g)/ Brain Wt (g) | 0.146 + 0.0434 | 0.076 + 0.0125 | 0.071 + 0.0090 | 0.074 + 0.0179 |

For each dose group, values are expressed as mean + standard errors, N = 3.
*Mean value signifcantly different from control mean at 5% level by Dunnett's test.
**Mean value significantly different from control mean at 1% level by Dunnett's test.

Since CI-977 is a very potent compound, very low doses can be administered.

CI-977 is not cytotoxic, a great advantage in pharmaceuticals. In the instant invention, both oral administration and continuous intravenous infusion were effective. In addition, desired prostatic effects were not dose-dependent, allowing one to administer lower doses of the compound and avoid unwanted side effects; CNS effects, or testicular effects, for example.

For the therapeutic uses described above, the usual mammalian dosage range for a 70-kg human subject is from 0.01 to 10 mg per day or 0.001 mg to 1.0 mg per kg of weight per day; optionally in divided portions. Determination of the proper dosage for a particular situation is within the skill of the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions, and suspensions and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at least 2% in a primarily liquid composition. The most satisfactory compositions are those in which a much higher proportion of the active ingredient is present.

Routes of administration of the subject compound or its salts are oral, parenteral, transdermal, or intranasal. For example, a useful intravenous dose is between 0.001 and 10 mg/kg. A preferred intravenous dose is 0.01 to 1 mg/kg. A still further preferred dose is 0.01 to 0.55 mg/kg. A useful oral dose is 0.01 to 30 mg/kg.

The following examples of formulations are provided to enable one skilled in the art to practice the invention. These examples are not intended to limit the scope of the invention in any way but rather to be illustrative thereof. All formulations are within the area of expertise of a skilled physician.

EXAMPLE 1

Injectables CI-977, Water for injection USP q.s.

The hydrochloride salt of Compound I is dissolved in water and passed through a 0.2-µ filter. Aliquots of the filtered solution are added to ampoules or vials, sealed, and sterilized.

EXAMPLE 2

Capsules 0.5 mg, 1 mg, or 2 mg

| CI-997 | 250 g |
|---|---|
| Lactose USP, Anhydrous q.s. or | 250 g |
| Sterotex Powder HM | 5 g |

Combine CI-977 and the lactose in a tumble, blend for 2 minutes, blend for 1 minute with the intensifier bar, and then tumble blend again for 1 minute. A portion of the blend is then mixed with the Sterorex Powder, passed through a #30 screen and added back to the remainder of the blend. The mixed ingredients are then blended for 1 minute, blended with the intensifier bar for thirty seconds, and tumble-blended for an additional minute. The appropriately sized capsules are filled with 141, 352.5, or 705 mg of the blend, respectively, for the 50-, 125-, and 250-mg containing capsules.

We claim:

1. A method of treating benign prostatic hypertrophy which comprises administering to a patient in need of said treatment a therapeutically effective amount of a compound in unit dosage form of the formula

1

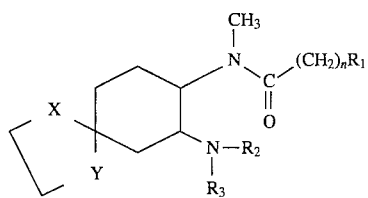

or a pharmaceutically acceptable salt thereof wherein n is an integer of from 1 to 6; either of X or Y is oxygen and the other is —CH$_2$—; R$_1$ is selected from a)

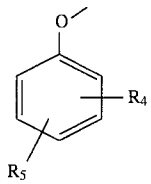

where R$_4$ and R$_5$ are independently hydrogen, fluorine, chlorine, bromine, nitro, trifluoromethyl, alkyl of from 1 to 6 carbon atoms, alkoxy of from 1 to 6 carbon atoms, or aryl;

b) 3,4,5-trimethylphenoxy;

c)

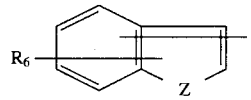

where R$_6$ is hydrogen, fluorine, chlorine, alkyl of from 1 to 6 carbon atoms, or aryl; Z is —CH$_2$—, —O—, —S—, or —NR$_7$— where R$_7$ is hydrogen, alkanoyl of from 1 to 6 carbon atoms, or alkyl of from 1 to 6 carbon atoms;

d)

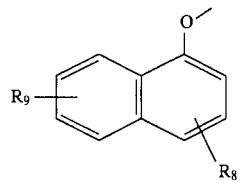

wherein R$_8$ and R$_9$ are independently hydrogen, fluorine, bromine, alkyl of from 1 to 6 carbon atoms, or alkoxy of from 1 to 4 carbon atoms; or e)

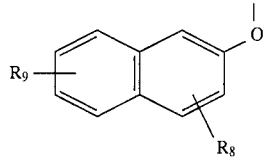

where R$_8$ and R$_9$ are as defined above;

where R$_2$ is methyl and R$_3$ is hydrogen, alkyl of from 1 to 6 carbon atoms,

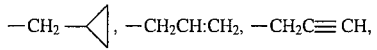

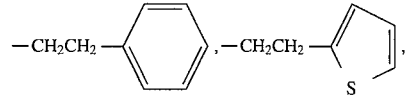

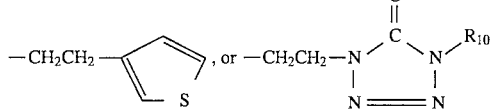

where R$_{10}$ is alkyl of from 1 to 4 carbon atoms; or where R$_2$ and R$_3$ when taken together with the nitrogen atom to which they are attached, form a pyrrolidinyl, piperidinyl, or hexahydro-1H-azepinyl ring.

2. A method according to claim 1 wherein the compound is (—)-5α-7α-8β-N-methyl-N-[7-(1-pyrrolidinyl)- 1-oxaspiro[4.5]dec-8-yl]-4-benzofuranacetamide.

3. A method according to claim 1 wherein the therapeutically effective amount is 0.001 mg to 10 mg/kg of weight per day of the compound or the pharmaceutically acceptable salt.

* * * * *